United States Patent [19]

Yang et al.

[11] Patent Number: 4,596,728
[45] Date of Patent: Jun. 24, 1986

[54] LOW TEMPERATURE HEAT SHRINKABLE POLYMER MATERIAL

[75] Inventors: Hou-Ching Yang, Hyattsville; Joseph Silverman, Silver Spring; John J. Wozniak, Columbia, all of Md.

[73] Assignees: The Johns Hopkins University, Baltimore; University of Maryland, College Park, both of Md.

[21] Appl. No.: 697,175

[22] Filed: Feb. 1, 1985

[51] Int. Cl.$^4$ ..................... F16L 11/04; A61B 12/04
[52] U.S. Cl. ..................... 428/36; 428/913; 128/334 C; 526/340.2; 138/177
[58] Field of Search ............... 423/36, 913; 174/DIG. 8; 526/340.2; 138/98, 103, 177; 128/334 C

[56] References Cited

U.S. PATENT DOCUMENTS 4,338,970  7/1982  Krackeler et al. ............ 174/DIG. 8
4,440,821  4/1984  Komura et al. ............... 174/DIG. 8
4,470,415  9/1984  Wozniak ....................... 128/334 R

OTHER PUBLICATIONS

Autian, *Toxicological Evaluation of Biomaterial*, Artificial Organics, vol. 1, pp. 53-60 (Aug. 77').

Primary Examiner—John E. Kitta
Assistant Examiner—James J. Seidleck
Attorney, Agent, or Firm—Robert E. Archibald; Mary L. Beall

[57] ABSTRACT

A heat shrinkable polymer material is particularly adapted for implanted biomedical use. A polycrystalline polymer is irradiated to produce crosslinking of its intramolecular structure to thereby impart viscoelasticity. The material is biocompatible and suitable for implanted use, from the standpoints of very low toxicity, ability to retain structural integrity and being non-carcinogenic and, moreover, is heat shrinkable at a temperature compatible with such implanted use.

18 Claims, No Drawings

LOW TEMPERATURE HEAT SHRINKABLE POLYMER MATERIAL

STATEMENT OF GOVERNMENTAL INTEREST

The Government has rights in this invention pursuant to contract N00024-81-C-5301 awarded by the Department of the Navy.

BACKGROUND OF THE INVENTION

This invention relates generally to polymer materials and more specifically to a crosslinked polymer particularly suitable for use in an implanted biomedical application.

The need currently exists for a low-toxicity, relatively low temperature, heat shrinkable polymer material capable of being used long-term in vivo, for example, as a connecting sleeve in a vascular anastomosis system, such as is disclosed in U.S. Pat. No. 4,470,415 issued to J. J. Wozniak. In that patent, a heat shrinkable sleeve material is placed over abutting ends of the vascular members to be joined; the respective ends of which have been prepared to be anastomosed by everting them over ferrule members placed over the ends of the vascular members. When the sleeve material is subjected to heat, it contracts and engages the vascular members and maintains them in firm connection.

Clearly, for such implanted biomedical applications as this, it is essential that the sleeve material have minimal toxicity and otherwise be compatible with implantation for the intended period of use, as well as being shrinkable at a temperature which is not so high as to cause necrosis of the adjacent body tissue. It should be understood, of course, that the proposed heat shrinkable material of the present invention has numerous applications, in addition to the implanted biomedical application such as that just described.

The crosslinking of polymeric substances by subjecting them to irradiation has been studied and utilized for several years, e.g. as a means of altering various structural parameters of the material. For example, A. Charlesby, in British Pat. No. 732047 published June 15, 1955, disclosed the treatment of polymeric substances to increase their resistance to organic solvents, by irradiating them with high energy electrons or gamma rays to thereby produce intramolecular bonds or crosslinks. Charlesby specifically disclosed the treatment of polyethylene, polystyrene, polyvinyl chloride, nylon, neoprene, gutta percha, smoked rubber, polyvinyl acetate, rubber hydrochloride and polyvinyl alcohol.

Similarly, W. A. Patterson, in U.S. Pat. No. 3,429,794, teaches a solvent shrinkable polymeric material produced by exposing the polymer to radiation from such sources as high energy electrons or the gamma rays from Cobalt 60 and then orienting it by stretching.

W. G. Baird, Jr., in U.S. Pat. No. 2,943,370, also teaches the use of high energy electrons and Cobalt 60 gamma rays to produce a heat shrinkable plastic made from polyethylene and useful for the production of document copies.

Other crosslinked polymers produced by irradiating the substance from a high energy source such as high voltage electrons or gamma rays, in order to enhance their physical or mechanical properties such as infusibility or solubility, are taught in the Charlesby et al U.S. Pat. No. 3,372,100; whereas, the manufacturer of a heat-recoverable crosslinked polymer of vinyl chloride and a polyunsaturated monomer are taught by Pinner in U.S. Pat. No. 3,359,193.

An implanted biomedical use of a heat shrinkable polymeric tube is taught by Bokros in U.S. Pat. No. 4,169,477, to join a vascular graft to the tubular portion of a prosthetic device; e.g. to allow accessing of a patient's blood system. In particular, this patent teaches the use of a copolymer of tetrachloroethylene and hexachloropropylene, trade-name TEFLON-FEP, which is described as being heat shrinkable at a temperature of approximately 300° F.

The above-described prior art thus teaches several heat shrinkable materials, but which for one reason or another are unsuitable for a significant number of biomedical and other applications. In particular, for implanted biomedical use, the heat shrinkable material must be biocompatible and, to enable a sleeve of the material to be applied in vivo, for example, as part of a vascular anastomosis procedure, it must be heat shrinkable at a temperature non-injurious to surrounding body tissue.

There are general criteria useful to assess the biocompatibility of the proposed heat shrinkable polymer for implanted use. First, the material must have low toxicity as regards local tissue response (necrosis or inflammation), systemic reaction and allergies, and be non-carcinogenic. Secondly, the polymer material must retain its structural form and perform its intended function over the anticipated life of the implant; specifically, the material must not dissolve or deteriorate when subjected to body fluids and enzymes. Finally, the temperature needed to initiate shrinkage and the duration of applied heat must not cause tissue necrosis. Conversely, the shrink temperature should be above normal body temperature and should also be selected to permit use in elevated temperature, e.g. tropical environments.

DESCRIPTION OF THE INVENTION

In accordance with the present invention, synthetic trans-1,4 polyisoprene (TPI), treated with irradiation to produce crosslinking in a particular method, has been found to be well suited for application to and use in an implanted biomedical environment. As a presently preferred embodiment, a synthetic trans-1,4 polyisoprene having the following structure has been utilized:

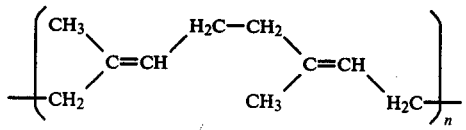

By way of example, this material is commercially available from Polysar, Inc. of Akron, Ohio (product code No. TP301) having a high (98%) trans content, as well as the following characteristics: specific gravity 0.96, crystalline melt temperature 58° C., crystallinity 30%, and molecular weight $4 \times 10^5$.

This synthetic trans-1,4 polyisoprene (TPI) material, selected and crosslinked in accordance with the present invention, has undergone a primary acute toxicity screening test performed pursuant a well-recognized protocol; see J. Autian, *Toxicological Evaluation of Biomaterials: Primary Acute Toxicity Screening Program*, published in Artificial Organics, Vol. 1, pp. 53–60 (August 1977). The proposed TPI material was found to have a Cumulative Toxicity Index (CTI) of 50 and, generally, any material having a CTI less than 100 is considered to have a low toxic liability. For example, a CTI of 50 is below that of silicone (CTI≈80) and slightly above polycarbonate (CTI≈30), both of which are used extensively for implants.

As regards its capability to retain structural integrity, in vivo, test samples of crosslinked TPI placed in intravenous (i.v.) saline at room temperature for approximately four months have not shown any change in mechanical strength, nor any hydrophilic (swelling by absorption of water) tendency. In addition, crosslinked TPI, implanted for twenty-one days in a practical application, did not appear to have undergone any significant physical change.

In a practical application of the proposed crosslinked TPI, as a sleeve material for use in performing sutureless vascular anastomosis as disclosed in the Wozniak U.S. Pat. No. 4,470,415, the TPI sleeve was shrunk by a jet of warm saline at 130° F. applied for approximately one second. No tissue damage due to this heat application was subsequently noted.

By way of background, potential application of trans-1,4 polyisoprene (TPI) to external orthopedic and rehabilitation medicine is described in an article by R. H. Jones and W. K. Wei, *J. Biomed. Mater. Res. Symposium*, Vol. 1, pp. 19-30 (1971), published by John Wiley & Sons, Inc. Potential external use for splints, braces, casts, and other orthopedic appliances are contemplated. As described by Jones and Wei, at room temperature, TPI exists as a crystalline rubber and that it is hard or semi-rigid at temperatures up to about 120° F. When heated to a range of 160°-180° F. the polymer becomes soft, plastic and self-adhering and its rate of crystallization is relatively slow at room temperature, rendering the polymer soft and moldable for some time at temperatures comfortable to the patient's skin. In other words, for the applications disclosed and contemplated by Jones and Wei, TPI would first be heated beyond its crystalline melt temperature, i.e. to 160°-180° F., and subsequently, during the interval when it is still soft and plastic and returning/cooling to a crystalline structure at room temperature, the material would be molded against the patient's body part to be supported or immobilized.

Other literature discussing the effects of radiation crosslinking on trans-1,4 polyisoprene (gutta percha) include: D. T. Turner, *Radiation Crosslinking of a Trans-1,4-Polyisoprene in the Liquid and Solid States*, Polymer Letters, Vol. 4, pp. 717-20 (1966) describing the effect on solubility, and R. P. Kusy and D. T. Turner, *Radiation Chemistry of Polymers Studied by Depression of Melting Temperature*, Radiation Chemistry, Vol. 4, No. 3 (May-June 1971) discussing the depression of crystalline melt temperature by gamma radiation.

In an article entitled *Radiation Processing: The Industrial Applications of Radiation Chemistry*, appearing in the Journal of Chemical Education, Vol. 58, p. 168 et. seq. (Feb. 1981), J. Silverman describes the basics of radiation crosslinking of polymeric materials, as well as some industrial applications for these materials. For example, heat shrinkable electrical connectors have been developed by Raychem Corp. and heat shrinkable packaging materials have been developed by the W. R. Grace Co. These products are based upon the viscoelastic memory feature of radiation-crosslinked polymers. As described at page 172 of this article, if the radiation-crosslinked product is first heated to the crystalline melting temperature, then stretched and quickly cooled in the stretched configuration, it will retain the distorted shape at room temperature. On subsequent heating of the polymer above the melting temperature, the crosslinks cause a rubber-like contraction of the film to its original form.

Fabrication Process

The preferred embodiment of the present invention will now be described as it would be applied to the fabrication of heat shrinkable sleeve members useful in the vascular anastomosis system disclosed in the Wozniak U.S. Pat. No. 4,470,415.

More particularly, the trans-1,4 polyisoprene (TPI) raw stock would initially be extruded in the form of tubing having an inside diameter equal to the desired diameter in the final shrunken tubing, i.e. firmly engaging the everted ends of the blood vessel(s) to be reconnected. By way of example, the tubing die used in conjunction with the extruder for one practical application produces tubing with an inside diameter of 4 millimeters and a wall thickness of 0.6 millimeters. Within the extruder, the TPI raw stock is heated to approximately 90° C. After the extruded tubing reaches room temperature it would be cut, if need be, into appropriate lengths and placed in a radiation cell chamber.

Exposing the tubing to ionizing radiation, e.g. produced from Cobalt 60 gamma rays (~1.2 MeV) or high energy electrons (0.2-10 MeV) developed with an electron accelerator, creates the intramolecular bonds known as crosslinks within the TPI. As is well-known, crosslinking with these sources does not induce radioactivity in the irradiated material. Crosslinking is preferably done in a vacuum at room temperature. In one practical application of the present invention, the exposure to gamma radiation in vacuum conditions was maintained at a dosage rate of 1.0 Mrad/hour, until a total dose of between 5 to 20 Mrad was achieved. In another set of experiments, irradiation in air with 7.2 MeV electron beams at a dosage rate of 28 Mrad/hr produced similar results in the same dose range.

After crosslinking, the tubing is post-irradiation annealed, in order to eliminate free radicals on or near the surface of the material which could react with oxygen in air and cause a degradation in the physical properties of the tubing with time. In practical application, TPI annealing was achieved by placing the crosslinked tubing in a water bath at 60° C. for 2 minutes.

Following the annealing step, the TPI material is exposed to a temperature at which the crystalline structure of the polymer is temporarily dissolved with heat, in order to allow the tubing to be mechanically expanded. In the case of TPI, the tubing is first placed in a water bath at about 130° F. and then forced onto a cylindrical rod or the like, with long tapered forward section, to accomplish the expansion. In one application of the present invention, the cylindrical portion of the rod has a diameter which is about two times the diameter of the extruded tubing. In order to facilitate insertion of the tapered rod into the polymer tubing, the rod may be first dipped in a liquid soap which acts as a lubricant. After the tubing is on the expanding rod, it is placed in cold water for approximately one minute (to re-crystallize the TPI), after which the expanded TPI tube can readily be slipped off the rod and any excess soap washed away with water. With a dose above 5 Mrad, the TPI tube will remain in this expanded state until it is reheated to the crystalline melt temperature of substantially 130° F. at which temperature it will have the same dimensions it had prior to expansion.

When utilized as a sleeve material in the anastomosis system disclosed in the Wozniak U.S. Pat. No. 4,470,415, an appropriate length of this TPI tubing, in its expanded state, would be disposed over the abutting ends of the blood vessels to be anastomosed and then subjected momentarily to an elevated temperature of 130° F., e.g. in the form of a warm saline jet. Thereupon, the crystalline structure within the TPI material temporarily dissolves and the tension in the crosslinks causes the tubing to return to its original, predetermined diameter established by the dimensions in the extruder die. In addition, some attendant reduction in length of the tubing also occurs, to thus draw the everted ends of the blood vessels into firm engagement with one another and to hold them there.

As noted previously, the present invention teaches for the first time that TPI can be utilized for implanted biomedical use, because of its good biocompatibility, it can be radiation-crosslinked to induce a viscoelastic memory, and moreover, it possesses a crystalline melt temperature which is compatible with biomedical applications, including use during surgery as a heat shrinkable, quick-acting connector. Thus, the fact that the melt temperature of TPI, for example, is approximately 130° F. allows such surgical connector to be shrink-applied in vivo, without damage to surrounding tissue during the procedure. Although other materials, e.g. the TEFLON-FEP connector disclosed in the Bokros U.S. Pat. No. 4,169,477, are also biocompatible, their required high heat shrink temperatures (300° F. and above) renders such materials unsuitable for many implanted uses, in that use of this temperature level during application of a connector in vivo would damage surrounding body tissue.

As noted previously, the proposed heat shrinkable TPI polymeric material has various other implanted biomedical applications, in addition to rejoining blood vessels as in the sutureless vascular anastomosis system covered by the Wozniak U.S. Pat. No. 4,470,415. For example, a heat shrinkable TPI sleeve might be used within the body in numerous anastomosis procedures, or for connecting prosthetics, or as a means for connecting external devices to human arteries, such as for chronic access for so-called left ventricular assist devices or for otherwise accessing the human blood system, similar to the coupling taught by the Bokros patent.

In addition, the proposed heat shrinkable TPI polymer material can be utilized as a shrinkable sleeve or covering that can be contracted underwater, since the water need only be heated locally to approximately 130° F. Other contemplated uses for the proposed heat shrinkable TPI material of the present invention include shrink tubing or film for electronics or foods sensitive to heat. Similarly, the relatively low shrink heat value renders the proposed TPI material suitable for toy or novelty items which can be made to contract, expand, unfold or otherwise assume a prior configuration (that during the crosslink formation), upon exposure to warm tap water; thus avoiding potential personal injury created by the high temperatures required to cause heat shrinking in other previously proposed crosslinked polymeric materials.

It should be understood at this time that the foregoing specification is directed at a preferred embodiment of the present invention and that various modifications, adaptations and alterations, over and above those described hereinabove, are of course possible within the scope of the present invention, as defined by the appended claims.

What is claimed is:

1. An article of manufacture comprising, a polycrystalline trans-1,4 polyisoprene having a crystalline melt temperature substantially 130° F. and produced by the sequential steps of: exposing the material to ionizing radiation sufficient to create intramolecular crosslinks within the material, heating the material to substantially 130° F., altering the shape of the material from a first configuration to a second configuration, and cooling the material while in said second configuration to re-form the crystalline structure, whereby said material will remain in said second configuration until subsequent reheating of the material to substantially 130° F. to cause the material to revert from said second configuration to said first configuration.

2. The article of manufacture specified in claim 1 wherein said trans-1,4 polyisoprene is composed of a trans constituent in excess of 90%.

3. A polycrystalline trans-1,4 polyisoprene, radiation-crosslinked to produce a viscoelastic memory therein and having a crystalline melt temperature of substantially 130° F. and being biocompatible.

4. The polycrystalline polymeric material specified in claim 3 wherein said trans-1,4 polyisoprene has a trans constituent in excess of 90%.

5. The polycrystalline polymeric material specified in claim 3 wherein the biocompatibility of said material is represented by a low-level toxicity and a retention of structural integrity while in vivo.

6. A heat shrinkable polymer material comprising, radiation-crosslinked, polycrystalline trans-1,4 polyisoprene characterized by a crystalline melt temperature of substantially 130° F. and pre-stretched to a first configuration, said polymer material shrinking to a second configuration upon the heating thereof to said crystalline melt temperature.

7. The heat shrinkable polymer material specified in claim 6 wherein said second configuration corresponds to a configuration of said material prior to stretching thereof to said first configuration.

8. The heat shrinkable polymer material specified in claim 7 wherein said second configuration is tubular and said first configuration is also tubular, but of a diameter larger than said second configuration.

9. The heat shrinkable polymer material specified in claim 6 wherein the trans-1,4 polyisoprene is synthetic and defined by the structural equation:

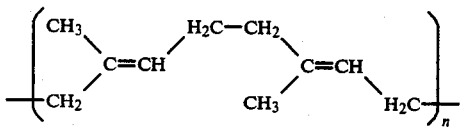

10. The heat shrinkable polymer material specified in claim 9 wherein said trans-1,4 polyisoprene has a trans constituent in excess of 90%.

11. The heat shrinkable polymer material specified in claim 6 having a viscoelastic memory characteristic causing said trans-1,4 polyisoprene to shrink from a first to a second configuration upon heating said polymer material to substantially 130° F.

12. The heat shrinkable polymer material specified in claim 11 wherein said viscoelastic memory is produced by the sequential steps of exposing the trans-1,4 polyisoprene to ionizing radiation sufficient to create intramolecular crosslinks within the material while the shape of said material is a first configuration, heating the material to substantially 130° F. to dissolve the crystalline structure of the material, stretching the heated material to a second configuration, and cooling the stretched material to reform the crystalline structure, whereby the material retains said stretched second configuration and whereby subsequent heating of the material to substantially 130° F. causes the material to return to its first configuration.

13. The heat shrinkable polymer material specified in claim 12, further comprising the step of annealing the material following said exposure to ionizing radiation and prior to stretching the material, by subjecting the material to a temperature of approximately 60° C. for substantially two minutes.

14. A heat shrinkable, biocompatible member useful for performing vascular anastomosis and like surgical procedures in vivo, comprising, a biocompatible, radiation-crosslinked polycrystalline trans-1,4 polyisoprene characterized by a crystalline melt temperature of substantially 130° F., said member being pre-stretched to a first configuration and capable of being movably disposed to encircle in sleeve-like fashion the vascular members to be interconnected and having a viscoelastic memory, whereby said pre-stretched member upon being heated to substantially 130° F. shrinks to a second configuration forming a sleeve of smaller diameter to engage and maintain said vascular members in interconnected relationship.

15. The heat shrinkable biocompatible member specified in claim 14 wherein said trans-1,4 polyisoprene is characterized by the structural equation:

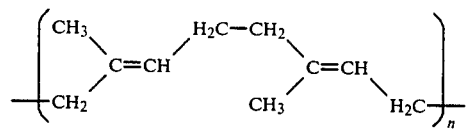

16. The heat shrinkable biocompatible member specified in claim 15 wherein the trans-1,4 polyisoprene is characterized by a trans constituent in excess of 90%.

17. The heat shrinkable biocompatible member specified in claim 15 wherein said trans-1,4 polyisoprene has a biocompatibility characterized by a low-level toxicity and a retention of structural integrity while in vivo.

18. The heat shrinkable biocompatible member specified in claim 14 wherein the first and second configurations of said member are tubular.

* * * * *